United States Patent
Bermpohl

(10) Patent No.: US 9,702,000 B2
(45) Date of Patent: Jul. 11, 2017

(54) USE OF PCR ANALYSIS FOR AIRBORNE NUCLEIC ACIDS

(71) Applicant: biotec Umwelt-Analytik-Beratung-Service GmbH, Guetersloh (DE)

(72) Inventor: Andreas Bermpohl, Guetersloh (DE)

(73) Assignee: biotec GmbH, Guetrsloh (DE)

( * ) Notice: Subject to any disclaimer, the term of this patent is extended or adjusted under 35 U.S.C. 154(b) by 74 days.

(21) Appl. No.: 14/636,262

(22) Filed: Mar. 3, 2015

(65) Prior Publication Data

US 2015/0247187 A1  Sep. 3, 2015

(30) Foreign Application Priority Data

Mar. 3, 2014 (DE) .......... 10 2014 203 855

(51) Int. Cl.
*C12Q 1/68* (2006.01)
*C07H 21/02* (2006.01)
*G01N 1/22* (2006.01)
*G01N 27/447* (2006.01)

(52) U.S. Cl.
CPC .......... *C12Q 1/686* (2013.01); *C12Q 1/6806* (2013.01); *G01N 1/2205* (2013.01); *G01N 1/2273* (2013.01); *G01N 27/447* (2013.01); *G01N 2001/2223* (2013.01)

(58) Field of Classification Search
CPC .... C12Q 1/6806; C12Q 1/686; G01N 1/2205; G01N 1/2273; G01N 2001/2223; G01N 27/447

See application file for complete search history.

(56) References Cited

PUBLICATIONS

Zhen, H. et al., Appl. Env. Microbiol., vol. 79, pp. 7780-7789 (Dec. 2013).*
Radosevich, J.L. et al., Lett. Appl. Microbiol., vol. 34, pp. 162-167 (2002).*
Makino, S.-I. et al., Lett. Appl. Microbiol., vol. 33, pp. 237-240 (2001).*
Lewandowski, R. et al., Environ. Monit. Assess., vol. 185, pp. 3517-3526 (Aug. 2012).*

* cited by examiner

*Primary Examiner* — Teresa Strzelecka
(74) *Attorney, Agent, or Firm* — Stacey J. Farmer; Grund IP Group

(57) ABSTRACT

The present invention relates to methods of analyzing airborne nucleic acid molecules using a device for the filtering and/or collecting of said molecules using an air sampling system, isolating the nucleic acids, and subsequent analysis thereof.

15 Claims, 3 Drawing Sheets

FIG 1: Schematic Representation of the MALDI-TOF-MS principle.
(A) Matrix-assisted laser desorption and ionization.
(B) Analysis of the molecular masses by time of flight.

USE OF PCR ANALYSIS FOR AIRBORNE NUCLEIC ACIDS

CROSS-REFERENCE TO RELATED APPLICATIONS

This application claims the benefit of German Patent Application DE 10 2014 203 855.3, filed on Mar. 3, 2014.

TECHNICAL FIELD

The present invention is in the field of bioanalytics. More specifically, the invention relates to the detection of airborne nucleic acid molecules.

BACKGROUND

The analysis of airborne nucleic acid molecules using conventional or real-time PCR methodologies is not currently applied worldwide due to a lack of sampling techniques and data extraction methods. However, there appear to be a variety of applications where such analytical approaches would be useful.

In all laboratories where the use of PCR technology is routinely used, a contamination problem commonly arises during the amplification of the same template DNA after a period of time. Due to aerosol generation (pipetting), the regular multiplication of the same nucleic acid regions results in amplicon contamination of the surrounding ambient air and wall surfaces. As a result, due to certain enrichment concentration over time, false-positive results occur since the airborne nucleic acids are able to enter those samples present in new analytical vessels. This situation has led to a required spatial separation of master mix preparations and the actual PCR being carried out, or to the necessary application of extra technical measures to prevent contamination of the preparations (i.e. PCR cabins). Such accumulated "contaminating" nucleic acid is to be expected not only in forensic laboratories, but also in laboratories dedicated to inspecting genetically modified food or feed. In the context of preventive quantitative analytics, it thus would seem desirable to routinely perform analysis of ambient air in order to determine the presence of contaminating nucleic acid fragments.

In addition to safeguarding quality-assurance procedures, another highly interesting field for airborne analytics emerges in the context of forensic analysis at crime scenes. When present in a room, every human being releases cellular material, and therefore clearly traceable genetic material, into the ambient air. Depending on the mode of human activity, said genetic material is released in lower or higher concentrations. Mere human presence leads to desquamation of the cornified stratified squamous epithelium of the skin, in addition to cellular material that is released into the ambient air due to coughing or sneezing reflexes via the mucous membranes; these secretions all contain personal nucleic acid components. If it were possible to reliably achieve enrichment of these genetic materials by air filtration, this would offer a unique forensic approach in addition to an effective searching strategy for detecting cellular or blood traces thus evidencing the presence of a specific person at a crime scene. However, to achieve this purpose, it would thus be necessary to directly filter large volumes of air on-site in order to deposit as much biological material as possible on a filter as derived from recently present persons. For example, air collection devices from the manufacturer Sartorius might enable a possibility of achieving sufficient biological concentrations on filter surfaces.

SUMMARY OF THE INVENTION

The present invention relates to a method for analyzing airborne nucleic acid molecules, the method comprising: filtering and/or collecting air using an air sampling system comprising an air filter and/or a collection medium, such that the nucleic acid molecules remain on the air filter and in said collection medium; isolating the nucleic acid molecules from the air filter and/or from the collecting medium; and analysis of nucleic acid molecules, preferably by PCR and subsequent gel electrophoresis.

The analysis can be carried out by PCR and subsequent gel electrophoresis, PCR and subsequent MALDI-TOF mass spectrometry and/or by in situ PCR.

In one embodiment, the air filter is a membrane filter made of nitrocellulose, wherein the pore size is from preferably 5 microns to 8 microns. In another embodiment, the air filter is a gelatin filter, wherein the pore size is from preferably 2 microns to 5 microns. In another embodiment, the collection medium is a suitable buffer, in which the nucleic acids/cells are collected by impaction. In another embodiment, the collection medium is a surface on which the nucleic acids/cells are deposited electrostatically or otherwise.

In one embodiment, the filter/collection medium can be decomposed into individual fragments on a contact-free basis by means of laser or mechanical device situated in a sterile housing unit, whereby the individual fragments are processed manually or automatically.

The air sampling system can be a Sartorius MD 8 system, an impaction system, or an electrostatic system.

In one embodiment, the inventive method is used for detecting contaminating nucleic acid molecules in a laboratory room, a production room, a storage room, or a lounge or a meeting room. The method can be used to obtain a human DNA profile from airborne human cellular material, or in the forensic analyses of crime scenes.

In one embodiment, the cellular material is dander or mucosal cells.

Furthermore, the invention also encompasses the use of an air sampling system comprising an air filter and/or a collecting medium for the analysis of airborne nucleic acid molecules. In one embodiment, the invention comprises the use of an air sampling system, comprising an air filter and/or a collection medium for obtaining a human DNA profile derived from airborne human cell material.

DESCRIPTION OF THE FIGURES (HEREINAFTER THE FIGURE LISTING)

Figure 4:
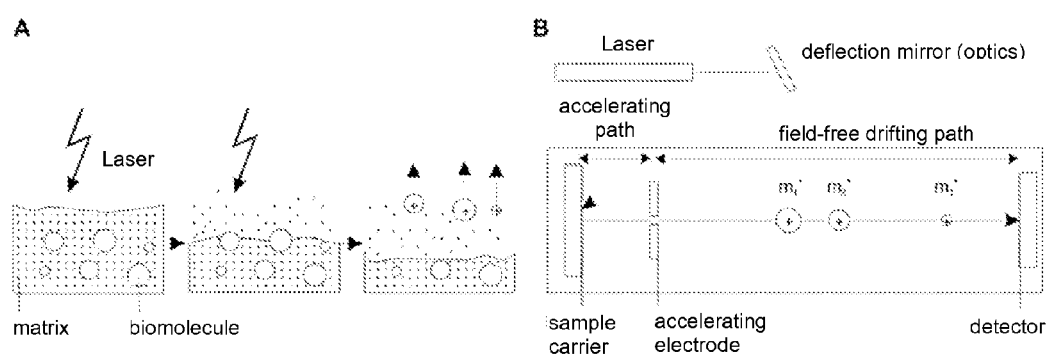

FIG. 4 schematically shows the principle of the analysis method using MALDI-TOF MS.

Figure 5:
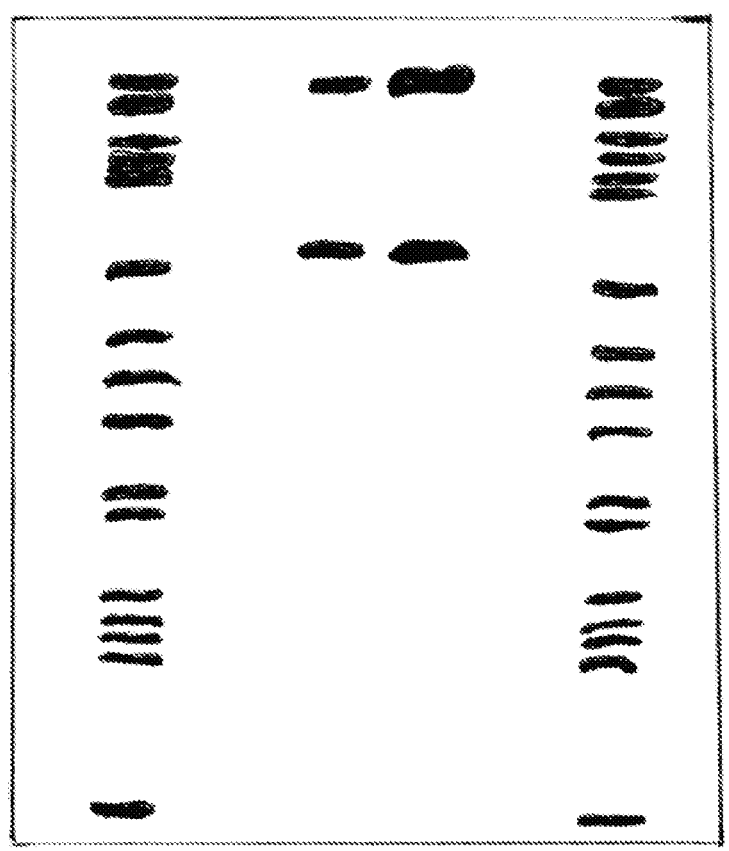

FIG. 5 shows agarose gel electrophoresis results: (left to right) marker, extraction of nitrocellulose, extraction of gelatin, marker

DETAILED DESCRIPTION OF THE INVENTION

Definitions

A "nucleic acid molecule" within the meaning of the invention, can be any nucleic acid molecule of any length. Examples of nucleic acids are deoxyribonucleic acids (DNA), ribonucleic acids (RNA) or peptide nucleic acids (PNA). Nucleic acids may be single-stranded, double-stranded, or partially single-stranded and partially double-stranded.

An "air sampling system" within the meaning of the present invention refers to any technical device that can be used to isolate non-gaseous constituents from the air. In particular, collection/filtration systems for air are contemplated, which can collect and deposit/intercept the particles from the air.

A "crime scene" within the meaning of the invention, is any place, e.g. closed rooms or outside, which was or likely was the scene of a crime or where a course of events is to be resolved.

The term "forensic analysis" refers to any investigation of a crime scene, in which the determination of the presence of a human or other living organism at a given moment in the past plays a role in the criminal event.

Methods

The present invention is based on the screening of various filter/collection-media/materials for air sampling and subsequent extraction/processing of the filter/collection media for subsequent PCR.

Figure 1:
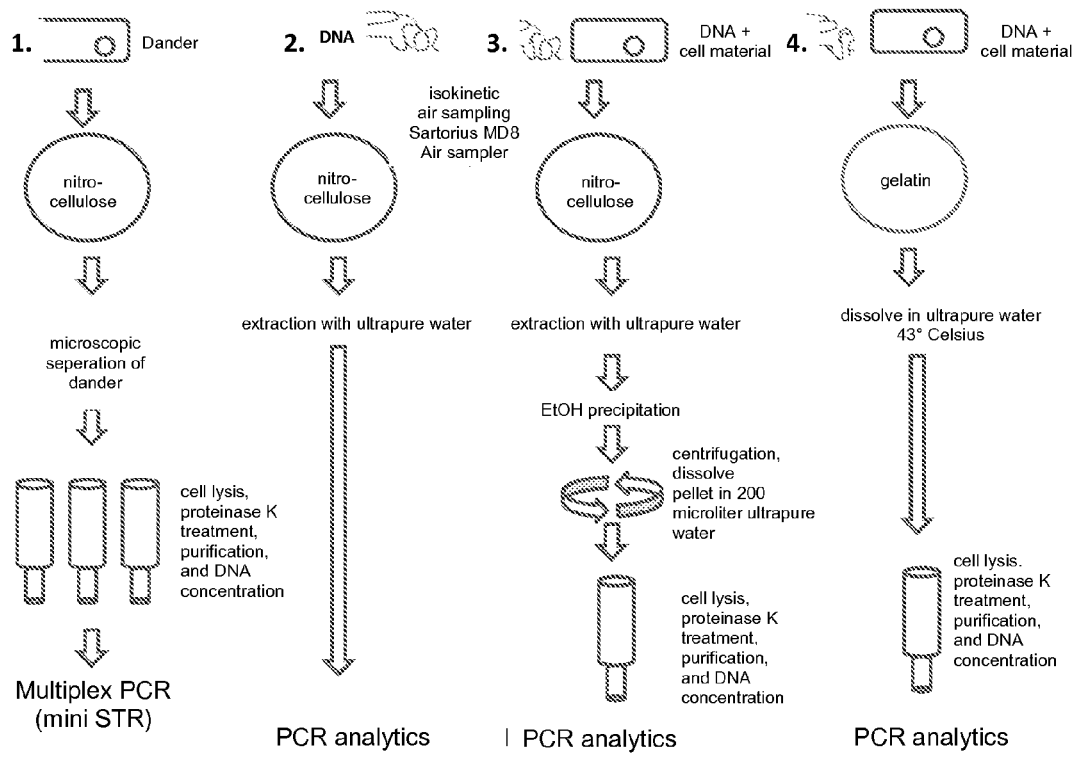
FIG. 1 shows processing schemes of four different embodiments of the invention.
Figure 2:
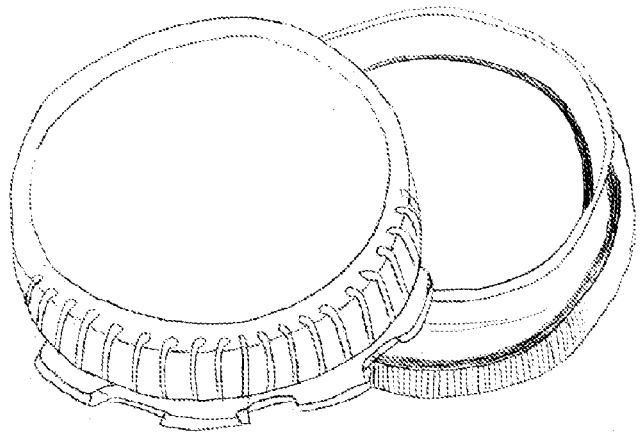
FIG. 2 shows an MD 8 air sampling system from the manufacturer Sartorius for filtration based on isokinetic sampling.
Figure 3:
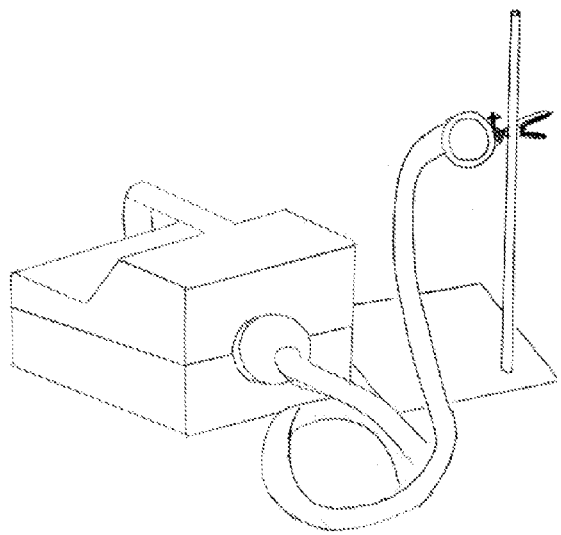
FIG. 3 shows an air filter for the MD 8 air sampling system from the manufacturer Sartorius with holders.

One inventive method comprises the filtration/collection of air that is suspected of containing air-borne nucleic acid molecules using an air sampling system that comprises: an air filter/a collection medium such that the nucleic acid molecules remain on the air filter/collection medium, or remain in the collection medium after filtering, respectively; isolating said nucleic acid molecules from the air filter/from the collecting medium or separating the nucleic acid molecules/cells deposited on the filter/collection medium and subsequent analysis of the nucleic acid molecules by means of a PCR reaction.

Air Sampling

Air sampling is used to deposit as much airborne nucleic acid as possible onto a filter surface or in/onto a matrix, for example, as derived from the biogenetic material of a person. Where appropriate, the air volume may be of a significantly high volume. Different air sampling systems are presently contemplated. In particular, membrane filtration may be used. Preferred is an air sampling system employing a suction power of at least 1 $m^3$/h, more preferably of at least 3 $m^3$/h. For example, the MD 8 isokinetic sampling system from the manufacturer Sartorius (see FIG. 2) can be used, wherein the air may be filtered through various filter matrices via an intake capacity of 6 $m^3$/h.

The duration of air sampling is dependent on the concentration of the airborne nucleic acids or on the biogenic materials containing them. Preferably, at least 5 $m^3$, at least 10 $m^3$, at least 15 $m^3$, at least 20 $m^3$, or at least 25 $m^3$ of air are filtered through the air sampling system.

Sampling can be carried out directly using a mobile stand, e.g., at a 1 m height positioned centrally in a room. To detect already sedimented biogenetic material, it is possible to disrupt any deposited sediment using ventilation techniques prior to subjecting this material to filtration. Alternatively, other known air sampling systems for sampling are contemplated: impaction (exchange of media against filters in empty petri dishes), impaction on other adsorptive surfaces, impinger methods, electrostatic air collectors, air scrubbers, mobile RLT systems with collective media such as air filters, etc.

Air Filter/Collecting Media

For the collection medium/air filter, both commercially available gelatin filters and nitrocellulose matrices are suitable. For gelatin filters, a pore size of 2 microns to 5 microns, more preferably about 3 microns, is preferred. For nitrocellulose filters, a pore size of 5 microns to 8 microns is preferred. Other matrices are conceivable, provided they can be adapted to the respective sampling system.

Isolation of Airborne Nucleic Acid Molecules

The isolation of the nucleic acid molecules from the air filters for further analysis can be carried out using means known in the art.

For the above-described embodiment relating to forensic analysis, dander e.g. as derived from a crime scene, is deposited on a nitrocellulose filter via filtration (see FIG. 1, column 1).

The collected dander is then separated from the filter/substrate surface, e.g. using a microscope, and then identified, with each individual sample being subjected to further processing.

A second separation technique involves fragmenting the filter/collection medium. For this purpose, a device can be used with which the filter/collection medium can be decomposed into smaller fragments in a contact-free manner using a laser or a mechanical device. The laser/mechanical device can be fixed to the filter/collection medium as the filter/collection medium is, e.g. being moved on an XY cross table. The movement of the XY cross table is achieved via two motor actuators, which can be controlled in using software, e.g. installed on a computer. The complete unit is housed in a sterile environment (e.g. a plexiglass cube with a sterile air supply). Using the described system, the dander fragments obtained from the filter/collection medium are available for further analysis.

Following the separation and processing of the collected dander, it is possible to obtain a complete nucleic acid profile using STR-profile based multiplex PCR. To this end, the cell membrane should be first solubilized by cell lysis. This may occur in 800 μl of a freshly prepared solution of 0.5 mg/ml lysozyme in TE buffer, pH 8.0. After addition of 80 μl of 10% SDS, the lysate is mixed well and incubated for 1-2 min in a water bath at 65° C. This procedure should yield a clear, viscous solution. Subsequently, 88 μl of an 1 M sodium acetate, pH 5.2 is added and mixed. The resulting cell lysate is then freed from proteins using proteinase K and subsequently purified. In the last step, the DNA is concentrated. This may be achieved via ethanol/isopropanol precipitation. To that end, the solution is mixed with 0.1 volume of an 3 M sodium acetate solution (final concentration 0.3 M) and 2 volumes of cold isopropanol. The precipitated DNA is then sedimented in a table-top centrifuge and the supernatant discarded. The DNA pellet is washed 1-2 times with 75% ethanol and dried. Subsequently, the DNA is taken up in distilled water or sterile buffer. All DNA enrichment/purification methods are suitable, including salt precipitation, phenol/chloroform extraction, columns and batch methods.

In another embodiment, nitrocellulose filters are used for the direct detection of free airborne nucleic acid molecules. The filters are easily extractable using sterile ultrapure water, thus offering the possibility of direct PCR analysis of the airborne nucleic acids (see FIG. 1, column 2).

In a further embodiment, cellular bound DNA is also integrated into the analysis. Here, the entire filter is extracted with a small volume of water. A first precipitation is then carried out using ethanol/isopropanol, whereby all free nucleic acids and cells are pelleted via high-speed centrifugation. The pellet is then dissolved, the cells are re-suspended, respectively, in 200 µl of ultrapure water, and the total volume is then used in the further purification steps. Similar to what was described for FIG. 1, column 1, a cell lysis, protein hydrolysis, and a concentration/precipitation is performed (see FIG. 1, column 3).

In another embodiment, a gelatin filter having a pore size of 3 microns is used as an air filter. In this embodiment, following filtration, the entire matrix is dissolved in ultrapure water at 43° C., and the gelatin is subsequently removed before PCR, e.g. by using a NucleoSpin Food extraction kit (Macherey-Nagel). Similar kits from other manufacturers are also suitable. The processing system used in this embodiment provides, in addition to the removal of all protein contaminants, the advantage that in addition to the enrichment of pure nucleic acid molecules, the release and purification of cellular nucleic acid can be also achieved (see FIG. 1, column 4).

Obtaining a Complete STR Profile from the Isolated Nucleic Acids

An STR ("short tandem repeat") profile can then be generated for the isolated nucleic acids. For this purpose, in one embodiment, an STR-multiplex PCR is performed and the resulting amplification product is analyzed using gel electrophoresis and subsequent computer evaluation (see Example 2).

Alternative: Reprocessing of the Analyte Using MALDI-TOF-MS

The analysis of the STR amplification product may also be achieved using MALDI-TOF mass spectrometry ("matrix assisted laser desorption/ionization—time off light").

For this purpose, as already described, amplicons obtained by PCR processing (STR regions) are mixed with a concentrated solution of the matrix. Here, the matrix molecules should exhibit an absorption maximum at the wavelength of the irradiated light. For the predominantly used UV-laser, 3-hydroxypicolinic acid is especially suitable for the DNA analysis step. After evaporation of the solvent, a semi-crystalline layer results, whereby the amplicon molecules are ideally completely separated from each other via matrix molecules. In the vacuum of the mass spectrometer, the amplicon is charged to 10 to 20 kV, and the matrix is then evaporated using laser pulses. An exact determination of an analyte's molecular mass is possible by accurately measuring the time it takes for an ion (amplicon) to fly through the field-free, defined drift region existing between the acceleration electrode and the detector.

As described below, in obtaining an STR-profile, a profile-to-person assignment is ultimately achieved by means of length polymorphisms at different genetic loci (STR regions) by matching to a database and/or to a control sample.

Alternative: Processing of the Analyte Using in Situ PCR

Additionally, processing of the biogenetic material is possible on the filter itself. Example 2 relates to a method of generating an STR profile from dander applied directly on a filter. Here, the genetic material situated on the filter is fixed using paraffin. In subsequent processing steps, especially during PCR, it is important to ensure that the substances used are protected from evaporation.

EXAMPLES

Example 1

Detection of Airborne Nucleic Acid Molecules Using an Air Sampling System

Air sampling systems fitted with air filters were tested to determine whether they can detect airborne nucleic acid molecules. Here, it is useful to consider both filter matrix alternatives described above (nitrocellulose and gelatin), especially since the gelatin filters have temperature- and moisture-related application limitations.

The extraction ability of the filter matrices was determined using "spotting experiments" wherein both filter matrices were loaded with template DNA of a known concentration, followed by extraction of the filter, and subsequent PCR. The sensitivity criteria of the tested filter matrices can also be determined by these experiments.

To test the suitability of the filter matrices for the analysis of airborne nucleic acid molecules, DNA aerosols were generated using a Pary-nebulizer, whose particle sizes are previously defined by particle monitoring. The aerosols were supplied by a ventilation system (air volume flow rate 300 $m^3$/h) of the isokinetic sampling air using membrane filtration using a Sartorius MD 8 system. The filters were then treated according to the following processing scheme, and then subjected to PCR.

The PCR samples were subjected to agarose gel electrophoresis for analysis, labeled using SYBR® Gold, and then photographed on a transilluminator. A standard size marker (250-10,000 bp) from Invitrogen was used.

Example 2

Obtaining a Complete STR Profile from Dander

Isolation of DNA

In order to obtain a sufficient amount of dander, air from a crime scene environment was first collected for a 3 hour period and filtered through a nitrocellulose filter at 6 $m^3$/h using a Sartorius MD 8 air sampling system. During the filtering, usually air from that specific room room is collected, but it is conceivable that the sampling of air from other indoor spaces may occur, e.g., air derived from nearby vehicles. Each obtained dander sampling was individually transferred from the filter with the aid of a light microscope and a micromanipulator under sterile conditions in a separate reaction vessel. Following the addition of 55 μl Chelex solution, 5% (Bio-Rad Laboratories, Hercules, Calif., USA) and 3 μl of proteinase K (10 IU/ml) (QIAGEN GmbH, Hilden, Germany), the samples were incubated in a thermal mixer at 37° C. and 450 rpm overnight (ca. 14 h). The samples were then boiled for 8 minutes at 93° C. and centrifuged at 13,000 rpm for 15 minutes. The Chelex-granule-free supernatant contained the DNA to be isolated.

STR Multiplex PCR

To select for successful extraction, 7 μl of each extract was used in a multiplex PCR with the cost-effective and highly sensitive Kit Q8 (in-house Short Tandem Repeat-PCR kit, University of Ulm, available without prescription) for 33 cycles using the following profile:

Hot start: 11 min at 95° C.

Denaturation: 1 min at 93° C.; 33 cycles

Annealing: 1 min at 59° C.

Elongation: 30 s at 72° C.

Final Elongation: 40 min at 72° C.

The Kit Q8 is a miniSTR-Multiplex-PCR kit containing shortened amplicons for the eight different German database systems D3S1358, FGA, TH01, VWA, SE33, D8S1179, D18551 and D21511 as well as the gender marker amelogenin. The following approach for a total volume of 10.9 µl each is used per reaction:

1.6 mM MgCl$_2$ (Applied Biosystems)
0.3 µl BSA (Boehringer Mannheim GmbH)
1.25 µl PCR buffer II (Applied Biosystems)
each 0.1 mM dNTPs
0.75 µl primer mix
2 U Ampli Taq Gold (Applied Biosystems)
1-7 µl DNA template
0-6 µl double-distilled water The subsequent purification of the PCR product was performed using the "QIAquick® PCR Purification Kit" (Qiagen, Hilden, Germany) according to the manufacturer's protocol. This system almost completely removes all enzymes, salts, oligomers, excess primers, nucleotides and various other foreign materials from the sample, and concentrates double-stranded DNA with a length of between 70 bp and 4 kb to a final volume of 9 µl.

For the electrophoresis, using an ABI Prism 3130 Genetic Analyzer (Applied Biosystems), each sample well was loaded with 10 µl Hidi™ formamide (Applied Biosystems), 0.5 µl standard GeneScan™ 500 ROX size standard (SERAC, Bad Homburg, Germany), and 1 amplicon, and boiled for 4 min at 94° C. Electrophoresis was carried out with the polymer POP7 (Applied Biosystems) with an injection time of 16 s, an injection voltage of 1.2 kV and a duration of 800 s. For the subsequent analysis, e.g. the software GeneMapperID v3.2 (Applied Biosystems) can be used.

Samples where not a single expected allele was detected are counted as empty. Samples containing more than two of the expected alleles, by contrast, are classified as useful for further investigation. For those samples where one or two of the expected alleles was detected, 7 µl extract is removed and subjected to a second round with the Q8-Kit for a further 33 cycles. If no correct allele was detected during the second round, the sample was also considered to be empty, but, on the other hand, where at least one correct allele was detected, this sample was subjected to subsequent processing by RT-PCR.

Quantification by Means of RT-PCR

For quantification using real-time PCR, the commercially available kit Plexor® HY (Promega) was applied on a 7500 Real Time PCR System (Applied Biosystems).

The Plexor® HY system is based on the interaction between two modified nucleotides. One of the PCR primers contains a nucleotide having a fluorescent iso-dC label. If the PCR is successful, the modified Dabcyl-iso-dGTP also contained in the PCR reaction mix, anneals to the above-mentioned primer and when inserted into the complementary DNA strand, leads to a decrease in fluorescence. By using different labels and primer sets, quantification of human DNA and human male DNA, and an assessment of possible inhibitors by an internal PCR control (IPC), is simultaneously possible. The target sequence of the autosomal primer labeled with the fluoresceine marker is a 99 bp long multi-copy sequence on chromosome 17 in the human RNU2 locus, which encodes an snRNA which is involved in the pre-mRNA processing. The Y-chromosomal primer is CAL Fluor® Orange 560-labeled and amplifies a 133-bp sequence of the testis-specific protein, which is part of the YSPY locus. CAL Fluor® 610 RED is a fluorescence marker for the IPC, IC5 is also included as a fourth label in all wells as a control reference. The 6.4 pg to 100 ng control standard enables a sensitivity sufficient to validate the quantification in the above-mentioned range. The implementation follows the requirements specified in the technical manual for an increase detectable in a sample extract volume from 2 to 3 µl. Accordingly, for each reaction, 10 µl of master mix, 1 µl primer/IPC Mix, 6 µl double-distilled water and 3 µl template DNA is used. Each sample was quantified in duplicate using two control standards and two empty controls per run. The PCR program consists of an initial denaturation at 95° C. for 2 min with subsequent 38 cycles of a 5 sec denaturation at 95° C. and a 35 s annealing and elongation at 60° C. Following the PCT protocols, the generated melting curves allows a control of the specificity of resulting products.

The invention claimed is:

1. A method for analyzing airborne nucleic acid molecules in airborne human cellular material, the method comprising:
   filtering and/or collecting air in an air sampling system that comprises an air filter and/or a collection medium, such that the nucleic acid molecules in the filtered/collected cellular material remain on the air filter and/or in the collection medium;
   isolating the nucleic acid molecules in the filtered/collected cellular material from the air filter and/or from the collecting medium;
   analyzing the isolated nucleic acid molecules; and
   obtaining a human DNA profile.

2. The method according to claim 1, wherein the air filter is a nitrocellulose membrane filter.

3. The method of claim 2, wherein the nitrocellulose membrane filter includes a pore size of between 5 µm to 8 µm.

4. The method according to claim 1, wherein the air filter is a gelatin filter.

5. The method according to claim 4, wherein the gelatin filter includes a pore size of between 2 µm to 5 µm.

6. The method according to claim 1, wherein the collection medium is a buffer for collecting the cellular material by impaction.

7. The method according to claim 1, wherein the collection medium is a surface on which the cellular material is deposited electrostatically.

8. The method according to claim 4, wherein the filter/collection medium is decomposed into individual fragments on a contact-free basis by means of a laser or mechanical device situated in a sterile housing unit, whereby the individual fragments are processed manually or automatically.

9. The method according to claim 1, wherein the air sampling system is a device for isolating non-gaseous constituents from the air.

10. The method according to claim 9, wherein the air sampling system is a Sartorius MD 8 system, an impaction system or an electrostatic system.

11. The method according to claim 1, wherein the filtering and/or collecting air is performed in a laboratory room, a production room, a storage room, a lounge, a meeting room or a crime scene.

12. The method according to claim 1, wherein the filtering and/or collecting air in the air sampling system occurs at a suction power of at least 1 m$^3$/h.

13. The method according to claim 12, wherein the air sampling system is the Sartorius MD 8 system and the suction power is 6 m$^3$/h.

14. The method according to claim 1, wherein at least 5 m$^3$ of air is filtered and/or collected through the air sampling system.

15. The method according to claim 1, wherein the filtering and/or collecting air is carried out using impaction, impinging methods, electrostatic air collectors, air scrubbers, or mobile RLT systems with collective media.

\* \* \* \* \*